United States Patent
Cuthbertson et al.

(10) Patent No.: US 8,216,548 B2
(45) Date of Patent: Jul. 10, 2012

(54) RADIOFLUORINATION METHODS

(75) Inventors: Alan Cuthbertson, Oslo (NO); Magne Solbakken, Oslo (NO); Hege Karlsen, Oslo (NO)

(73) Assignee: GE Healthcare AS, Oslo (NO)

(*) Notice: Subject to any disclaimer, the term of this patent is extended or adjusted under 35 U.S.C. 154(b) by 322 days.

(21) Appl. No.: 12/518,728

(22) PCT Filed: Dec. 27, 2007

(86) PCT No.: PCT/US2007/088890
§ 371 (c)(1),
(2), (4) Date: Jun. 11, 2009

(87) PCT Pub. No.: WO2008/083191
PCT Pub. Date: Jul. 10, 2008

(65) Prior Publication Data
US 2010/0034740 A1    Feb. 11, 2010

(51) Int. Cl.
*A61K 51/00*    (2006.01)
(52) U.S. Cl. ............ 424/1.89; 424/1.69; 514/543
(58) Field of Classification Search ............ 424/1.11, 424/1.69, 1.89; 514/543
See application file for complete search history.

(56) References Cited

U.S. PATENT DOCUMENTS
7,368,474 B2 * 5/2008 Cuthbertson et al. ......... 514/453

FOREIGN PATENT DOCUMENTS
WO    2006/030291    3/2006

OTHER PUBLICATIONS

Olberg, D. et.al. "A novel prosthetic group for site-selective labeling of peptides for positron emission tomography" Bioconjugate Chemistry 200806 US, vol. 19, No. 6, Jun. 2008, pp. 1301-1308.
Carrasco, M. et.al. "Chemoselective alkylation of N-alkylaminooxy-containing peptides" Organic Letters Aug. 3, 2006, vol. 8, No. 16, pp. 3529-3532.
Bark, S. et.al. "A highly efficient method for site-specific modifcation of unprotected peptides after chemical synthesis" Journal of the American Chemical Society, Washington, DC., vol. 122, No. 15, Apr. 19, 2000, pp. 3567-3573.

* cited by examiner

*Primary Examiner* — Michael G Hartley
*Assistant Examiner* — Jagadishwar Samala

(57) ABSTRACT

The invention relates to conjugates of formula (V) or (VI), their use as radiopharmaceuticals, processes for their preparation, and synthetic intermediates used in such processes.

9 Claims, No Drawings

RADIOFLUORINATION METHODS

FIELD OF INVENTION

The present invention relates to diagnostic and radiodiagnostic agents, including biologically active vectors labelled with positron-emitting nuclides. It further relates to methods and reagents for [$^{18}$F]-fluorination of vectors, where a vector is defined as a molecule with an affinity for a specific biological target, and is preferably a peptide. The resultant $^{18}$F-labelled conjugates are useful as radiopharmaceuticals, specifically for use in Positron Emission Tomography (PET).

BACKGROUND OF THE INVENTION

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases.

One difficulty with $^{18}$F-labelled peptides is that the existing $^{18}$F-labelling agents are time-consuming to prepare. Efficient labelling of peptides and proteins with $^{18}$F is only achieved by using suitable prosthetic groups. Several such prosthetic groups have been proposed in the literature, including N-succinimidyl-4-[$^{18}$F]fluorobenzoate, m-maleimido-N-(p-[$^{18}$F]fluorobenzyl)-benzamide, N-(p-[$^{18}$F]fluorophenyl) maleimide, and 4-[$^{18}$F]fluorophenacylbromide. Almost all of the methodologies currently used today for the labeling of peptides and proteins with $^{18}$F utilize active esters of the fluorine labelled synthon. As peptides and proteins may contain a multitude of functional groups capable of reaction with active esters these current methods are not site-specific. For example a peptide containing three lysine residues has three amine functions all equally reactive towards the labelled synthon. Therefore, there still exists a need for $^{18}$F-labelled prosthetic groups and methodologies, which allow rapid, chemoselective introduction of $^{18}$F, particularly into peptides, under mild conditions to give $^{18}$F-labelled products in high radiochemical yield and purity. Additionally, there is a need for such methodologies which are amenable to automation to facilitate preparation of radiopharmaceuticals in the clinical setting. Although we have previously described the use of aminoxy chemistry in PET labelling strategies (WO 2004/080492 A1), the compounds of this invention do not react readily aldehydes and ketones but are selective for some halogen-containing compounds. The greater chemical stability of the N-alkylaminoxy moiety provides an advantage over the aminoxy group previously disclosed as side-reactions are minimised and intermediates are more stable which aids successful handling and storage of intermediates.

DETAILED DESCRIPTION OF THE INVENTION

The present invention provides a method for radiofluorination comprising reaction of a compound of formula (I) with a compound of formula (II):

or,
a compound of formula (III) with a compound of formula (IV)

wherein
R1 is an halogen-containing moiety, such as a haloacetyl or phenacylhalide and R2 is an N-alkyl-aminooxy group which, under mild conditions such as aqueous buffer and slightly acidic pH reacts site-specifically with R1 yielding a stable conjugate.

R3 is an N-alkyl-aminooxy group capable of reacting site-specifically with R4. In this case R4 is a is a halogen-containing moiety, such as a haloacetyl or phenacylhalo group capable of reacting with the N-alkyl-aminoxy group of vector V; to give a conjugate of formula (V) or (VI) respectively:

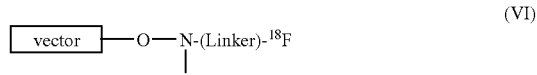

wherein Y is alkyl or aryl but preferably methyl and the $^{18}$F-Linker group in the compounds of formulae (II) and (V) is selected from a group of synthons comprising an N-alkyl aminoxy moiety linked to the $^{18}$F atom via stable bonds preferably comprising the formulas:

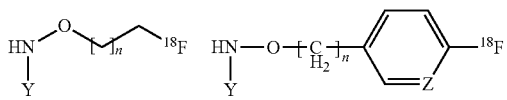

and the $^{18}$F-Linker group in the compounds of formula (IV) and (VI) is selected from the halogen-containing synthons preferably but not exclusively comprising the formulas

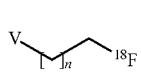 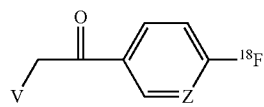

wherein:
V is a halogen atom preferably bromine, chlorine or iodine
n is an integer of 0 to 20;
Z is O, N or S.

The Linker group in the compounds of formulae (II), (IV), (V) and (VI) may be chosen to provide good in vivo pharmacokinetics, such as favourable excretion characteristics in the resultant conjugate of formula (V) or (VI). The use of linker groups with different lipophilicities and or charge can significantly change the in vivo pharmacokinetics of the peptide to suit the diagnostic need. For example, where it is desirable for a conjugate of formula (V) or (VI) to be cleared from the body by renal excretion, a hydrophilic linker is used, and where it is desirable for clearance to be by hepatobiliary excretion a hydrophobic linked is used. Linkers including a polyethylene glycol moiety have been found to slow blood clearance which is desirable in some circumstances.

This reaction may be effected in a suitable solvent, for example, in an aqueous buffer in the pH range 3 to 11, and at a non-extreme temperature of from 5 to 70° C., preferably at ambient temperature.

The present invention provides a more chemoselective approach to radiolabelling where the exact site of introduction of the label is pre-selected during the synthesis of the peptide or vector precursor. The ligation reaction occurring at a pre-determined site in the molecule and gives only a single labeled product. This methodology is therefore chemoselective, and its application is considered generic for labeling a wide range of drug-like molecules, peptides biomolecules such as small proteins.

In a further aspect, the present invention provides a method for radiofluorination comprising reaction of a compound of formula (Ia) with a compound of formula (IIa):

$$R1 - \boxed{vector} \quad (Ia)$$

$$^{18}F\text{-(Linker)-O} - NH - CH_3 \quad (IIa)$$

or,
a compound of formula (IIIa) with a compound of formula (IVa)

$$H_3C - \underset{H}{N} - O - \boxed{vector} \quad (IIIa)$$

$$^{18}F\text{-(Linker)-R4} \quad (IVa)$$

wherein R1 and R4 are as defined above for the compounds of formula (I) and (IV) respectively; the Linker group in the compounds of formulae (IIa) and (IVa) are each a $C_{1-60}$ hydrocarbyl group, suitably a $C_{1-30}$ hydrocarbyl group, optionally including 1 to 30 heteroatoms, suitably 1 to 10 heteroatoms such as oxygen or nitrogen. Suitable Linker groups include alkyl, alkenyl, alkynyl chains, aromatic, polyaromatic, and heteroaromatic rings, and polymers comprising ethyleneglycol, amino acid, or carbohydrate subunits; to give a conjugates of formula (Va) or (VIa) respectively:

$$^{18}F\text{-(Linker)-O} - \underset{|}{\overset{CH_3}{N}} - \boxed{vector} \quad (Va)$$

$$\boxed{vector} - O - \underset{|}{\overset{|}{N}}\text{-(Linker)-}^{18}F \quad (VIa)$$
$$\phantom{vector - O - }CH_3$$

wherein the Linker group is as defined for the compound of formula (IIa) or (IVa).

The term "hydrocarbyl group" means an organic substituent consisting of carbon and hydrogen, such groups may include saturated, unsaturated, or aromatic portions.

In a preferred aspect, the present invention provides a method for radiofluorination comprising reaction of a compound of formula (VIIa):

$$\boxed{vector} - O - NH - Y \quad (VIIa)$$

with a compound of formula (VIIb)

$$^{18}F\text{-Linker-V} \quad (VIIb)$$

and more specifically some preferred examples of (VIIb) are represented in formulas (VIII), (IX) or (X):

$$^{18}F - (CH_2CH_2O)_n CH_2CH_2 - NHCOCH_2 - Br \quad (VIII)$$

$$^{18}F \underset{}{\overset{}{\diagup\diagdown}}_n \overset{Br}{\diagdown} \quad (IX)$$

$$^{18}F - \underset{}{\bigcirc} - \underset{O}{\overset{}{C}} - CH_2Br \quad (X)$$

wherein:
n is an integer of 0 to 20;
Y is an alkyl or aryl substituents
to give a compounds of formula (VIIc)

$$^{18}F\text{-Linker-NH(Y)-O-Vector} \quad (VIIc)$$

or preferably conjugates of formula (XII-XV) respectively:

$$^{18}F\text{-}(CH_2CH_2O)_n CH_2CH_2\text{-NHCOCH}_2\text{-N(Y)-O-Vector} \quad (XII)$$

$$^{18}F\text{-}(CH_2)_n N(Y)\text{-O-Vector} \quad (XIII)$$

$$^{18}F\text{-}(C_6H_4)\text{-CO-CH}_2\text{-N(Y)-O-Vector} \quad (XIV)$$

This reaction may be effected in a suitable solvent, for example, in an aqueous buffer in the pH range 3 to 11, and at a non-extreme temperature of from 5 to 70° C., preferably at ambient temperature.

In a further preferred aspect, the present invention provides a method for radiofluorination comprising reaction of a compound of formula (XVa):

$$V - \boxed{vector} \quad (XVa)$$

where V is a halogen preferably with compounds of the general formula (XVb)

$$^{18}\text{F-Linker-O-NH(Y)} \qquad \text{(XVb)}$$

and preferably with compounds of the formula (XVI), (XVII),(XVIII)

$$^{18}\text{F}-(\text{CH}_2-\text{CH}_2-\text{O})_n-(\text{CH}_2)_m-\text{O}-\text{NH}-\text{CH}_3 \qquad \text{(XVI)}$$

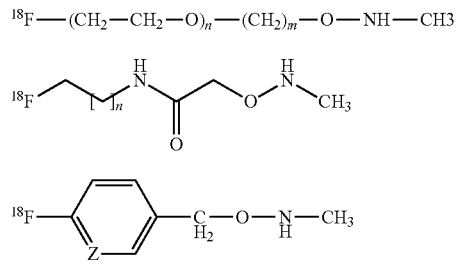

(XVII)

(XVIII)

wherein Y, m and n are as defined for the previous compounds.

The reaction may be effected in a suitable solvent, for example, in an aqueous buffer in the pH range 3 to 11, and at a non-extreme temperature of from 5 to 70° C., preferably at ambient temperature.

In formulae (I) and (III) and in other aspects of the invention unless specifically stated otherwise, suitable vectors for labelling are peptides, which may include somatostatin analogues, such as octreotide, bombesin, vasoactive intestinal peptide, chemotactic peptide analogues, α-melanocyte stimulating hormone, neurotensin, Arg-Gly-Asp peptide and its analogues, human pro-insulin connecting peptide, endothelin, angiotensin and formyl-norleucyl-leucyl-phenylalanyl-norleucyl-tyrosyl-lysine. Preferred peptides for labelling are Arg-Gly-Asp peptide and its analogues, such as those described in WO 01/77415 and WO 03/006491. Preferred peptides comprise the fragment:

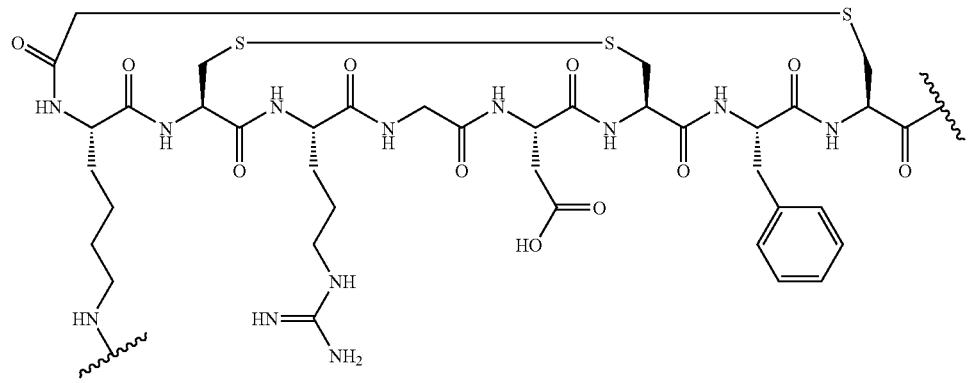

In one particular aspect, the peptide in formula (I) or (III) is of formula (A):

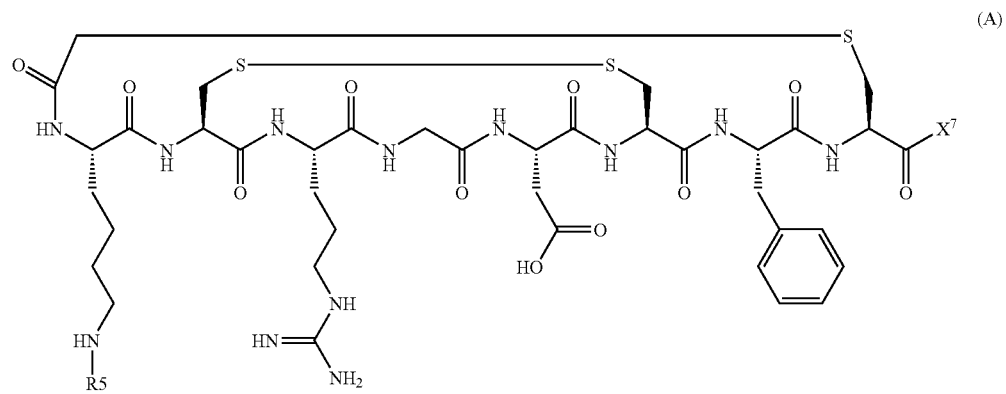

(A)

wherein $X^7$ is either $-NH_2$ or

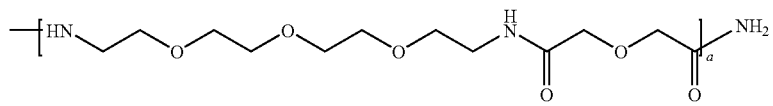

wherein a is an integer of from 1 to 10, preferably a is 1. and R5 is a halogen containing moiety suitable for reaction with the 18F-labeled synthons of formula (III) or a moiety containing an N-alkylaminooxy substituent capable of reacting with a synthon of formula (I).

As will be appreciated by the skilled person, the methods of the invention may also be used for radiofluorination of other biomolecules such as proteins, hormones, oligonucleotides, and antibody fragments, as well as small drug-like molecules to provide a variety of PET tracers.

Compounds of formula (I) and (III) may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the group R1 and R3 in a compound of formula (I) or (III) may be achieved by reaction of the N or C-terminus of the peptide or with some other functional group contained within the peptide sequence, modification of which does not affect the binding characteristics of the vector. In a preferred example the N-alkylaminoxy-contaning function, $Y-NH_2-O-$, may be directly introduced into the peptide sequence using the amino acids described by Carrasco et al (Biopolymers, Peptide Science, 2006, Vol 84 (4), page 414). The functional groups R1 and R3 are preferably introduced by formation of a stable amide bond formed by reaction of a peptide amine function with an activated acid and introduced either during or following the peptide synthesis. When the precursor is an acid then R1 and R3 can be introduced using in situ activating agents such as 2-(1H-benzotriazole-1-yl)-1,1,3,3-tetramethyluronium hexafluorophosphate (HBTU) or N-[dimethylamino)-1H-1,2,3-triazolo[4,5-b]pyridin-1-ylmethylene]-N-methylmethanaminium hexafluorophosphate N-oxide (HATU).

Compounds of formula (II) may be prepared from the corresponding precursors of formula (XIX):

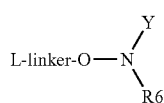

(XIX)

wherein L is a leaving group preferably a p-toluenesulphonate, trifluoromethanesulphonate, or methanesulphonate or a halide and Y and Linker are as defined previously and where R6 is a suitable protecting group for protection of the nitrogen atom such as the t-butyloxycarbonyl group and where by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 150° C., suitably 60 to 120° C. or by microwave heating, followed by removal of any N-protecting group using standard methods such as acidolytic treatment.

Compounds of formula (IV) may be prepared from the corresponding precursors of formula (XX):

 

(XX)

or a protected derivative thereof, wherein L is a leaving group preferably a p-toluenesulphonate, trifluoromethanesulphonate, or methanesulphonate or a halide and the Linker is as defined previously and V is a reactive halogen moiety with selectivity towards N-alkylaminoxy substituents and is preferably a bromine-containing unit by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 120° C.

The present invention also provides a radiopharmaceutical composition comprising an effective amount (e.g. an amount effective for use in in vivo PET imaging) of a compound of general formula (V) or (VI), together with one or more pharmaceutically acceptable adjuvants, excipients or diluents.

A preferred embodiment of the invention relates to a compound of general formula (V) or (VI), for medical use and particularly for use in tumour imaging (suitably by PET); wherein the vector is an Arg-Gly-Asp peptide or an analogue thereof, such as those described in WO 01/77415 and WO 03/006491, preferably a peptide comprising the fragment

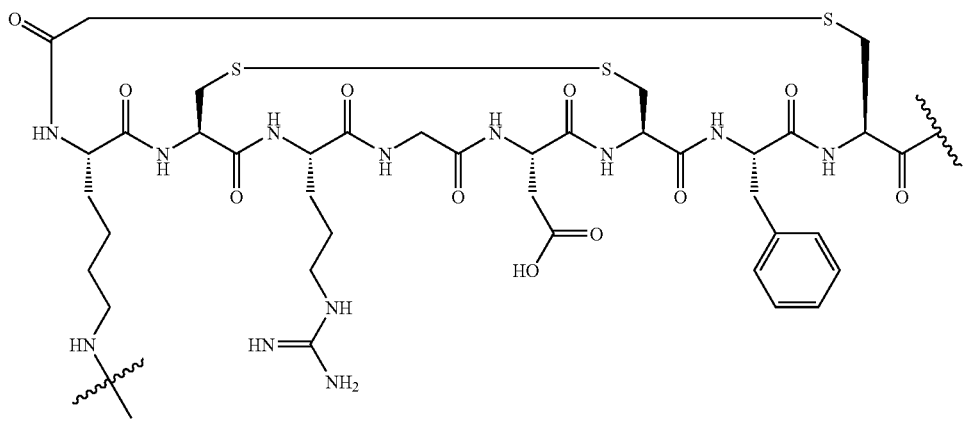
more preferably the peptide of formula (A):
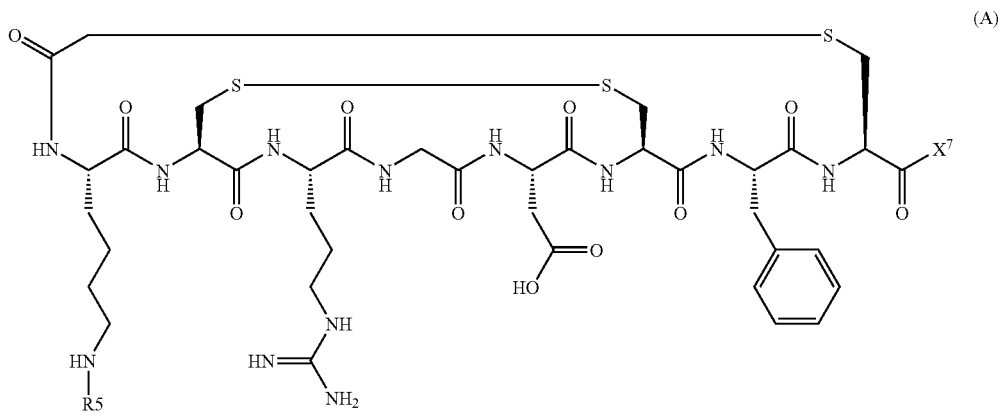
wherein X⁷ is either —NH₂ or
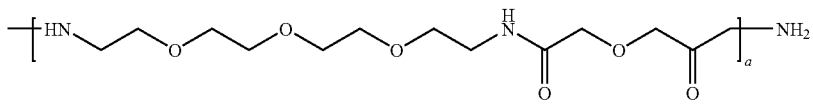
wherein a is an integer of from 1 to 10, preferably a is 1 and where R5 forms an amide bond or a secondary amine bond with the ε-amino of the lysine residue following reaction of the peptide and is preferably chosen from the list i-v and vii-viii below.
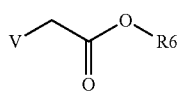
i
-continued
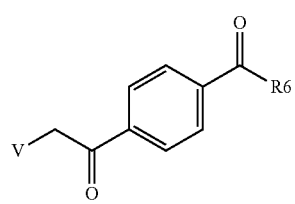
ii
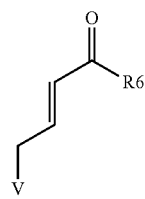
iii

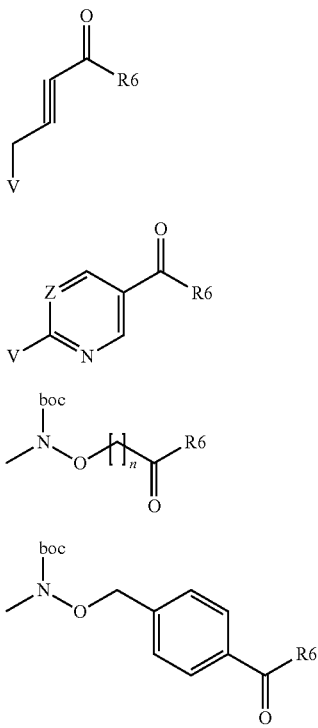

where R6 is an active ester activating group such as an N-hydroxysuccinimide or acid chloride and V is a halogen, preferably bromine, chlorine or iodine.

The radiolabelled conjugates of the invention may be administered to patients for PET imaging in amounts sufficient to yield the desired signal, typical radionuclide dosages of 0.01 to 100 mCi, preferably 0.1 to 50 mCi will normally be sufficient per 70 kg bodyweight.

The radiolabelled conjugates according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Viewed from a further aspect the invention provides the use of a radiolabelled conjugate of the invention for the manufacture of a radiopharmaceutical for use in a method of in vivo imaging, suitably PET, and preferably for tumour imaging; involving administration of said radiopharmaceutical to a human or animal body and generation of an image of at least part of said body.

Viewed from a still further aspect the invention provides a method of generating an image of a human or animal body involving administering a radiopharmaceutical to said body, e.g. into the vascular system and generating an image of at least a part of said body to which said radiopharmaceutical has distributed using PET, wherein said radiopharmaceutical comprises a radiolabelled conjugate according to the invention.

Viewed from a further aspect the invention provides a method of monitoring the effect of treatment of a human or animal body with a drug to combat a condition associated with cancer, preferably angiogenesis, e.g. a cytotoxic agent, said method comprising administering to said body a radiolabelled conjugate according to the invention and detecting the uptake of said conjugate by cell receptors, preferably endothelial cell receptors and in particular αvβ3 receptors, said administration and detection optionally but preferably being effected repeatedly, e.g. before, during and after treatment with said drug.

In yet another embodiment of the instant invention, there is provided a kit for the preparation of a radiofluorinated tracer comprising a prosthetic group of formula (II) or (IV) and a compound of formula (I) or (III).

According to a further aspect of the invention, there is provided a kit for the preparation of a radiofluorinated tracer comprising a prosthetic group of formula (XIX) and a compound of formula (I). According to another aspect of the invention, there is provided a kit for the preparation of a radiofluorinated tracer comprising a prosthetic group of formula (XX), and a compound of formula (III).

In use of the kits, the compound of formula (XIX) would be converted to the corresponding compound of formula (II) and the compound of formula (XX) would be converted to the corresponding compound of formula (IV), respectively, using methods described above. Preferably, the compound of formula (II) and (IV) may be separated from waste reactants by passing the reaction mixture through a Solid Phase Extraction (SPE) cartridge. The SPE cartridge may comprise a graphite pad, $C_{18}$ stationary phase or ion exchange resin. The compound of formula (II) and (IV) would then be added to the compounds of formula (I) and (III) respectively which may suitably be dissolved in aqueous buffer (pH 3-11). After reaction at a non-extreme temperature for 1 to 70 minutes, the labelled peptide may be purified, for example, by SPE and collected.

EXAMPLES

The invention is further described in the following examples which are in no way intended to limit the scope of the invention.

The invention is illustrated by way of examples in which the following abbreviations are used.

HPLC: high performance liquid chromatography

NMR: nuclear magnetic resonance hr(s): hours(s)

min(s): minutes(s)

THF: tetrahydrofuran

DCM: dichloromethane

DMF: N,N-dimethylformamide

TBAF: tetrabutylammonium fluoride

MeOH: methanol

DMSO: Dimethylsulphoxide

Boc: t-butoxycarbonyl

RT: room temperature i-Pr$_2$-Net: N,N-Diisopropylethylamine t-BDPSiCl: tert-butyldiphenylsilyl chloride NaH: Sodiumhydride EtOAc: Ethyl acetate MBq: Mega becquerel

Example 1

Preparation of Toluene-4-sulfonic acid 4-(N-Methyl-N-Boc-aminooxy)-butyl ester

Compound 1

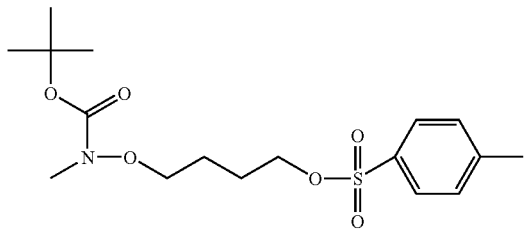

(a) N-Boc-N-methylhydroxylamine

N-methyl-hydroxylamine (4.2 g, 0.05 mol) was dissolved in a 50% aqueous tetrahydrofuran (THF) (20 ml) and cooled on ice while stirring. Potassium carbonate (3.6 g, 0.0275 mol) was added to the ice-cooled solution followed by di-tert-butyl dicarbonate (12 g, 0.055 mol) dissolved in 15 ml THF. The mixture was stirred at 0° C. for 2 hours and at room temperature for 2 hours. The THF was removed under reduced pressure and the residue was dissolved in DCM. The solution was washed two times with water, dried (MgSO$_4$), and concentrated giving a pink low viscous oil of 6.47 g(88%). The product was identified by electrospray mass spectrometry (ESI-MS)(MH$^+$ calculated 147.09; found 147.6). The product was used in without further purification.

(b) (4-bromo-butoxy)-tert-butyl-diphenyl-silane

To a solution of 4-bromo-1-butanol (2.75 g, 18 mmol) in DCM (10 ml) containing i-Pr$_2$-Net (10 ml) was added t-BDP-SiCl (5 ml, 18 mmol) under argon atmosphere. The solution was stirred at room temperature for 2 hours, concentrated in vacuo, and chromatographed (Hexane/ethyl acetate 10:1). Giving a low viscous colour free oil of 4.39 g (62%). Structure confirmed with NMR.

(c) O-[4-(tert-butyl-diphenyl-silanyloxy)-butyl]-N-methyl-N-Boc-hydroxylamine N-Boc-N-methylhydroxylamine (a) (0.74 g, 5 mmol) was dissolved in 10 ml DMF, treated with NaH (200 mg, 60% dispersion in mineral oil, 4.75 mmol), and stirred for 1 h under an argon atmosphere. The mixture was cooled to 0° C., treated with a solution of 4-bromo-butoxy)-tert-butyl-diphenyl-silane (b) (1.56 g, 4 mmol) in DMF (10 mL) and stirred at 0° C. for an additional 3 hours. The solvents were removed under reduced pressure, and the residue was dissolved in EtOAc (150 mL) and poured into a separatory funnel. The organic layer was washed with 0.1 M NaOH (5×50 mL), H$_2$O (50 ml), 0.1 M KHSO$_4$, and brine (50 ml) and the dried with MgSO$_4$. After removal of the solvent, the residue was chromatographed on silicagel(Hexane:EtOAc 10:1) to yield 0.588 g (24%). The product was identified by electrospray mass spectrometry (ESI-MS)(MFE calculated 457.26; found 457.8)

(d) 4-(N-methyl-N-Boc-hydroxylamine)-butan-1-ol

TBAF (1.6 mL, 1.586 mmol) was added to O-[4-(tert-butyl-diphenyl-silanyloxy)-butyl]-N-methyl-N-Boc-hydroxylamine (c)(588 mg, 1.22 mmol) dissolved in dry THF 20 mL. The reaction was stirred over night under argon. NH$_4$Cl (saturated) was added to the solution (10 mL×3) and the THF was evaporated. The solution was extracted with DCM, the organic phase was dried (Na$_2$SO$_4$) and evaporated. The residue was chromatographed (Hexane/EtOAc 1:1) on silicagel to give 0.170 g (63%). The product was analyzed by HPLC (column:Phenomenex Luna 3µ C18 (2), 4.6×50 mm, detection: 214 nm, gradient: 50%-100% B over 10 min where A=H$_2$O/0.1% TFA and B=acetonitrile/0.1% TFA, flow rate: 2 mL/min, Rt=2.70 min) Further confirmation was carried out by NMR analysis.

(e) Toluene-4-sulfonic acid 4-(N-methyl-N-Boc-hydroxylamine)-butyl ester

To a ice bath cooled stirred solution of 4-(N-methyl-N-Boc-hydroxylamine)-butan-1-ol (d) (170 mg, 0.77 mmol) and triethylamine (161 µL, 1.155 mmol) in dry DCM 10 mL was added toluene-4-sulfonylchloride (190.8 mg, 1.001 mmol) in dry DCM (5 mL) under argon. The ice bath was removed after 15 minutes and the reaction mixture was left at room temperature. After 2 hours new reagents were added (triethylamine (32 µL, 0.23 mmol), toluene-4-sulfonylchloride (29.36 mg, 0.154 mmol). After 24 hours presumed product can be observed on TLC. 30 hours: New reagents were added to the reaction mixture (triethylamine (53 µL, 0.385 mmol), toluene-4-sulfonylchloride (73.5 mg, 0.385 mmol) and left over night. The organic phase was washed with 10% NaHCO$_3$ (10 mL×3) and dried with MgSO$_4$. The organic phase was removed under vacuum and flashed on silica (hexane:ethyl acetate 6:4) giving 111 mg (41.5%) of product. NMR revealed impurities of toluene-4-sulfonylchloride in product. Further purification was needed to remove 4-sulfonylchlodride. Using n-hexane:EtOAc (8:2) better separation was achieved on a silica flash column and the 4-sulfonylchloride was removed. Yield: 64 mg (22%). The product was analyzed by HPLC (column:Phenomenex Luna 3µ C18 (2), 4.6×50 mm, detection: 214 nm, gradient:20%-80% B over 10 min where A=H$_2$O/0.1% TFA and B=acetonitrile/0.1% TFA, flow rate: 2 mL/min, Rt=2.70 min). The product was identified by electrospray mass spectrometry (ESI-MS)(MH$^+$ calculated 373.16; found 373.9) Further confirmation was carried out by NMR analysis.

Example 2

Preparation of O-(4-fluoro-butyl)-(N-methyl-N-Boc-hydroxylamine) as cold standard Compound 2

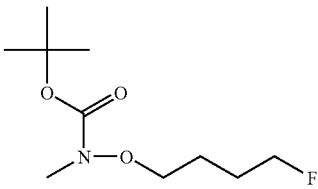

KF (4.64 mg, 0.080 mmol) and kryptofix (30.1 mg, 0.080 mmol) was dissolved in dry acetonitrile (0.75 mL). The mixture was stirred for 5 min after which compound 1 (15 mg, 0.040 mmol) dissolved in dry acetonitrile (0.250 mL) was added under argon. The mixture was heated at 60° C. for 1 hour. After one hour TLC showed that the reaction was completed. The solvent was evaporated and the residue was flashed on silicagel hexane/EtOAc(1:1) affording 4.5 mg (51%). The product was analyzed by HPLC (column:Phenomenex Luna 3μ C18 (2), 4.6×50 mm, detection: 214 nm, gradient:20%-70% B over 10 min where A=$H_2O$/0.1% TFA and B=acetonitrile/0.1% TFA, flow rate: 2 mL/min, Rt=2.70 min). The product was identified by electrospray mass spectrometry (ESI-MS)($MH^+$ calculated 221.14; found 221.7). Structure confirmed with NMR.

Example 3

Radiosynthesis of $^{18}$F-compound 2 and conjugation to 2-bromo acetophenone

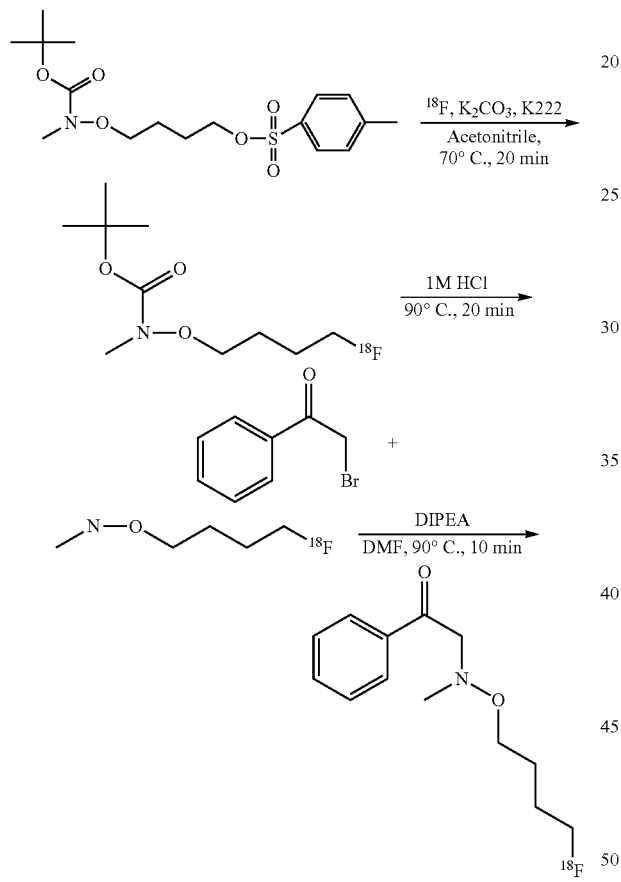

Radio synthesis was performed on SynChrom R & D module from Raytest.

$^{18}$F-fluoride (up to 1 GBq) was azeotropically dried in the presence of Krytptofix 222 (39.1 mg in 1 mL acetonitrile) and potassium carbonate (65.7 mg in 1 mL water) by heating under $N_2$ to 90° for 9 minutes. During this time 2×1 mL acetonitrile were added and evaporated. After cooling to <40°, a solution of toluene-4-sulfonic acid 4-(N-Methyl-N-Boc-aminooxy)-butyl ester (compound 1) (3 mg in 1 mL acetonitrile) was added. The reaction vessel was heated to 70° C. for 20 minutes to effect labelling. The crude reaction mixture was injected to HPLC at 214 nm, with an isocratic flow using 60/40 $CH_3CN/H_2O$. Chromatogram showed good yields of the labelled compound about 86% RCP co-eluting with cold standard. The crude reaction mixture was eluted through a Sep-Pak aluminium column using 2 mL of ACN to remove free fluoride, the activity of the free fluoride was measured (less than 15% contributed by free fluoride). The "purified" mixture was reanalysed on HPLC, to see free fluoride is removed. 1 mL (100 MBq) of the purified product was hydrolysed in 1 mL 1 M HCl for 20 minutes at 90° C., to remove the BOC-protecting group, giving 100% of the unprotected F-18 radiolabelled compound. 1 mL of the hydrolysed product was diluted with 10 mL of milli-Q water and the pH was adjusted to pH 11-12 and eluted through a pre-conditioned SEP-PAK C-18 column. The activity on the column was measured to be 30.1 MBq. The column was eluted with 2 mL DMF into a reaction vial giving 2 mL with 23 MBq. 6 mg bromo-acetophenone was added with 10 μL diisopropyl ethyl amine and heated at 90° C. for 10 minutes. The reaction mixture was analyzed by HPLC showing evidence of conjugate formation by a new peak eluting at 5.46 minutes with a greater area (57%) than the peak corresponding to the "free" precursor. HPLC (column: Xterra (waters) 5μ C18 4.6×250 mm, detection: 250 and 214 nm, NaI detector Gradient: Isocratic; 40% A=$H_2O$ and 60% C=acetonitrile flow rate: 1 mL/min)

Specific Embodiments, Citation of References

The present invention is not to be limited in scope by specific embodiments described herein. Indeed, various modifications of the inventions in addition to those described herein will become apparent to these skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method for radiofluorination comprising reaction of a compound of formula (I) with a compound of formula (II):

(I)

(II)

or, a compound of formula (III) with a compound of formula (IV)

(III)

(IV)

wherein

R1 is a halogen-containing moiety;

R2 is an N-alkyl aminooxy group;

R3 is an N-alkyl aminoxy group; and

R4 is a is a halogen-containing moiety;

to give a conjugate of formula (V) or (VI) respectively:

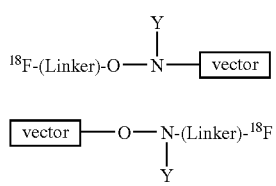

(V)

(VI)

wherein Y is alkyl or aryl and the $^{18}$F-Linker group in the compounds of formulae (II) and (V) is selected from a group of synthons comprising an N-alkyl aminoxy moiety linked to the $^{18}$F atom via stable bonds and the $^{18}$F-Linker group in the compounds of formula (IV) and (VI) is selected from the halogen-containing synthons.

2. A method of claim 1, wherein R1 is a haloacetyl or phenacylhalo group.

3. A method of claim 1, wherein R4 is a haloacetyl or phenacylhalo group.

4. A method of claim 1, wherein Y is methyl.

5. A method of claim 1, wherein the $^{18}$F-Linker group in the compounds of formulae (II) and (V) is selected from

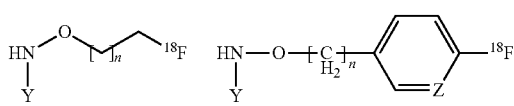

wherein:
Y is alkyl or aryl;
n is an integer of 0 to 20; and
Z is O, N or S.

6. A method of claim 1, wherein the $^{18}$F-Linker group in the compounds of formula (IV) and (VI) is selected from

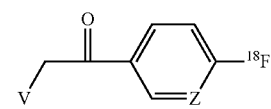

wherein:
V is a halogen atom preferably bromine, chlorine or iodine
n is an integer of 0 to 20; and
Z is O, N or S.

7. A method of claim 1, wherein the vector is Arg-Gly-Asp peptide or an analogue thereof.

8. A method of claim 7, wherein the vector comprises the fragment

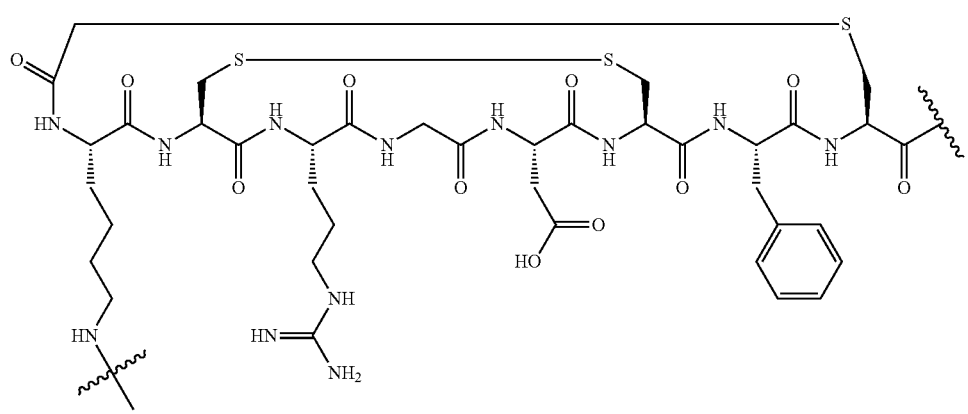

9. A method of claim 7, wherein the vector is formula (A):

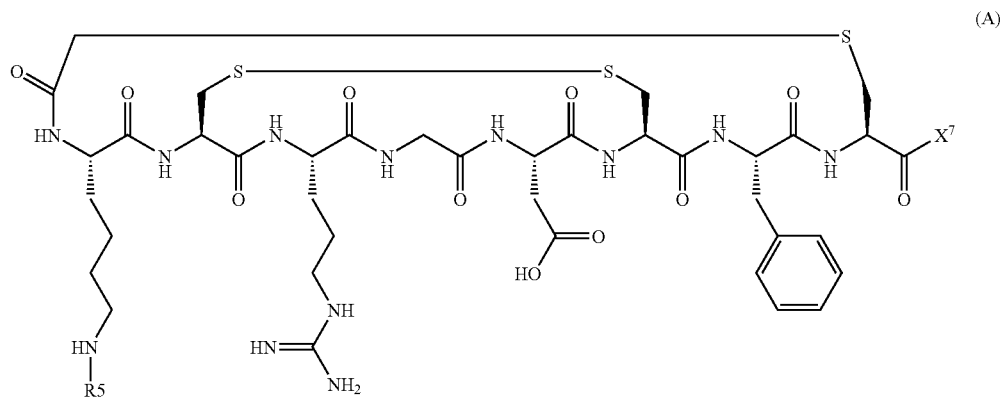

wherein $X^7$ is either —$NH_2$ or

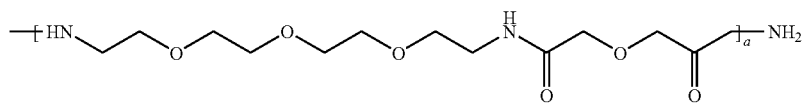

wherein a is an integer of from 1 to 10, and where R5 forms an amide bond or a secondary amine bond with the ε-amino of the lysine residue following reaction of the peptide and is preferably chosen from the list i-vii below

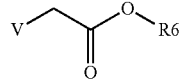 i

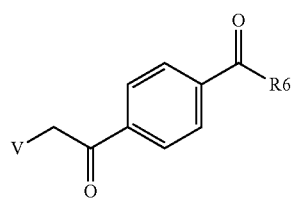 ii

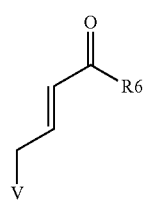 iii

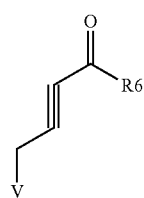 iv

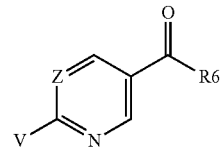 v

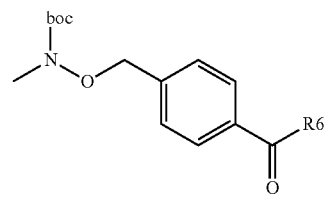 vi

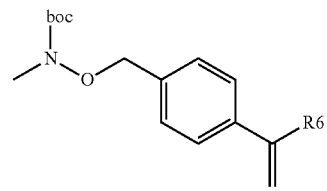 vii wherein R6 is an active ester activating group such as an N-hydroxysuccinimide or acid chloride and v is a halogen atom preferably bromine, chlorine or iodine.

* * * * *